United States Patent [19]

Scherkenbeck et al.

[11] Patent Number: 5,334,608
[45] Date of Patent: Aug. 2, 1994

[54] AZOLYMETHYL-CYCLOPROPYL DERIVATIVES

[75] Inventors: Jürgen Scherkenbeck, Leverkusen; Thomas Himmler, Odenthal; Hermann Hagemann, Leverkusen; Stefan Dutzmann, Hilden; Heinz-Wilhelm Dehne, Monheim; Gerd Hänssler, Leverkusen, all of Fed. Rep. of Germany

[73] Assignee: Bayer Aktiengesellschaft, Leverkusen, Fed. Rep. of Germany

[21] Appl. No.: 21,390

[22] Filed: Feb. 23, 1993

[30] Foreign Application Priority Data

Mar. 2, 1992 [DE] Fed. Rep. of Germany ....... 4206529

[51] Int. Cl.$^5$ ................. A01N 43/653; C07D 249/08
[52] U.S. Cl. .................................. 514/383; 514/184; 548/101; 548/267.4; 548/267.6
[58] Field of Search .............. 548/101, 267.4, 267.6; 514/184, 383

[56] References Cited

U.S. PATENT DOCUMENTS 4,639,527 1/1987 Lantzsch et al. ............... 548/267.8
5,059,615 10/1991 Fugmann et al. ............... 548/267.8

FOREIGN PATENT DOCUMENTS 0106515 9/1983 European Pat. Off. .
180850 10/1985 European Pat. Off. .
297345 6/1988 European Pat. Off. .

OTHER PUBLICATIONS

Chemical Abstracts, vol. 112, No. 19, May 7, 1990, Abstract No. 178,994w.

*Primary Examiner*—Patricia L. Morris
*Attorney, Agent, or Firm*—Sprung Horn Kramer & Woods

[57] ABSTRACT

New azolylmethyl-cyclopropyl derivatives of the formula

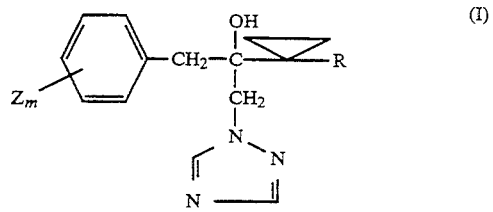

in which
R represents cyano or a group of the formula

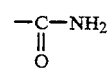

Z represents halogen, alkyl having 1 to 4 carbon atoms, halogenoalkyl having 1 to 4 carbon atoms and 1 to 5 halogen atoms, alkoxy having 1 to 4 carbon atoms, halogenoalkoxy having 1 to 4 carbon atoms and 1 to 5 halogen atoms, or alkoximininoalkyl having 1 to 4 carbon atoms in the alkoxy group and 1 to 4 carbon atoms in the alkyl group and
m represents the numbers 0, 1 or 2, and addition products thereof with acids or metal salts are very effective for combating fungi.

New oxiranes of the formula

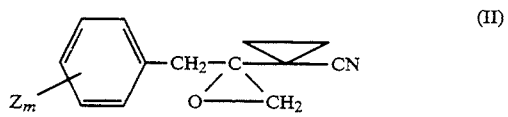

in which
Z and m have the abovementioned meanings, are valuable intermediates for the preparation of compounds of the formula (I).

3 Claims, No Drawings

AZOLYMETHYL-CYCLOPROPYL DERIVATIVES

The present invention relates to new azolylmethyl-cyclo-propyl derivatives, to a process for their preparation, and to their use as fungicides.

It has already been disclosed that certain hydrox ethylazolyl derivatives have fungicidal properties (cf. EP-OS (European Published Specification) 0,106,515). For example, 2-(4-chlorophenyl)-1-(1,2,4-triazol-1-yl)-3-cyano-3-methyl-butan -2-ol and 2-(2,4-dichlorophenyl)-1-(1,2,4-triazol-1-yl) -3-methyl-3-carboxamido-butan -2-ol can be used for con, Dating fungi. The action of these substances is good, but leaves something to be desired in some cases when the application rates are low.

New azolylmethyl-cyclopropyl derivatives of the formula

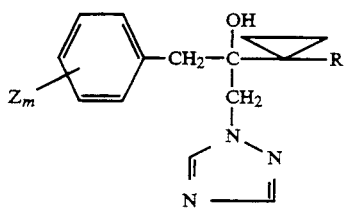

in which

R represents cyano or a group of the formula

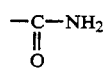

Z represents halogen, alkyl having 1 to 4 carbon atoms, halogenoalkyl having 1 to 4 carbon atoms and 1 to 5 halogen atoms, alkoxy having i to 4 carbon atoms, halogenoalkoxy having 1 to 4 carbon atoms and 1 to 5 halogen atoms, or alkoximinoalkyl having 1 to 4 carbon atoms in the alkoxy group and 1 to 4 carbon atoms in the alkyl group and m represents the numbers 0, 1 or 2, and their acid addition salts and metal salt complexes, have now been found.

Furthermore, it has been found that azolylmethyl-cyclo-propyl derivatives of the formula (I) and their acid addition salts and metal salt complexes are obtained when, in a first step, oxiranes of the formula

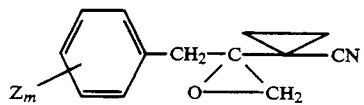

in which

Z and m have the abovementioned meanings, are reacted with 1,2,4-triazole of the formula

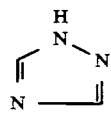

if appropriate in the presence of an acid-binding agent and in the presence of a diluent, and, if appropriate, the resulting compounds of the formula

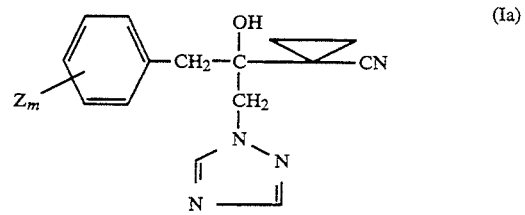

in which

Z and m have the abovementioned meanings, are treated, in a second step, with hydrogen peroxide in the presence of an inert organic diluent and in the presence of an aqueous alkali metal hydroxide solution as well as in the presence of a phase transfer catalyst, and, if appropriate, an acid or a metal salt is subsequently added onto the compounds of the formula (I) thus obtained.

Finally, it has been found that the new azolylmethyl-cyclopropyl derivatives of the formula (I) and their acid addition salts and metal salt complexes have very good fungicidal properties.

The substances according to the invention contain an asymmetrically substituted carbon atom. They can therefore be obtained in the form of optical isomers. The present invention relates to the individual isomers as well as to their mixtures.

Surprisingly, the substances according to the invention have better fungicidal properties than 2-(4-chlorophenyl) -1-(1,2,4-triazol-1-yl)-3-cyano-3-methyl-butan -2-ol and 2-(2,4-dichlorophenyl)-1-(1,2,4-triazol-1-yl) -3-methyl-3-carboxamido-butan -2-ol, which are previously known active substances having a similar constitution and the same direction of action.

Formula (I) provides a general definition of the azo-lyl-methyl-cyclopropyl derivatives according to the invention.

R represents cyano or a group of the formula

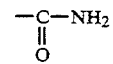

preferably represents fluorine, chlorine, alkyl having 1 or 2 carbon atoms, halogenoalkyl having 1 or 2 carbon atoms and 1 to 3 identical or different halogen atoms, alkoxy having 1 or 2 carbon atoms, halogenoalkoxy having 1 or 2 carbon atoms and 1 to 3 identical or different halogen atoms, or alkoximinoalkyl having 1 or 2 carbon atoms in the alkoxy group and 1 or 2 carbon atoms in the alkyl group.

m preferably represents the numbers 1 or 2.

particularly preferably represents fluorine, chlorine, methyl, trifluoromethyl, methoxy, trifluoromethoxy, methoximino-methyl or ethoximinomethyl.

Other preferred substances according to the invention are addition products of acids with those azolyl-methyl-cyclo-propyl derivatives of the formula (I) in which R, Z and m have the meanings given above as being preferred.

The acids which can be added on include, preferably, hydrohalic acids such as, for example, hydrochloric acid and hydrobromic acid, in particular hydrochloric acid, furthermore phosphoric acid, nitric acid, sulphuric acid, mono- and bifunctional carboxylic acid and hydroxycarboxylic acids such as, for example, acetic acid, maleic acid, succinic acid, fumaric acid, tartaric acid, citric acid, salicylic acid, sorbic acid and lactic acid as well as sulphonic acids such as, for example, p-toluenesulphonic acid, 1,5-naphthalenedisulphonic acid or camphor-sulphonic acid, saccharin and thiosaccharin.

Other preferred compounds according to the invention are addition products of salts of metals of main group II to IV and sub-group I and II as well as IV to VIII of the Periodic System of Elements with those azolylmethyl-cyclopropyl derivatives of the formula (I) in which R, Z and m have the meanings given above as being preferred.

Salts of copper, zinc, manganese, magnesia, tin, iron and of nickel are particularly preferred here. Suitable anions of these salts are those which are derived from those acids which lead to physiologically acceptable addition products. Particularly preferred acids of this type are, in this context, the hydrohalic acids such as, for example, hydrochloric acid and hydrobromic acid, furthermore phosphoric acid, nitric acid and sulphuric acid.

Examples which may be mentioned of azolylmethyl-cyclo-propyl derivatives of the formula (I) are the substances listed in the table below.

TABLE 1

(I)

| $Z_m$ | R |
|---|---|
| 4-Cl | —CN |
| 4-Cl | —CO—NH$_2$ |
| 4-F | —CO—NH$_2$ |
| 4-F | —CN |
| 2,4-Cl$_2$ | —CN |
| 2,6-Cl$_2$ | —CN |
| 2-CH$_3$ | —CN |
| 2-CH$_3$ | —CO—NH$_2$ |
| 2-CF$_3$ | —CN |
| 2-CF$_3$ | —CO—NH$_2$ |
| 4-CF$_3$ | —CN |
| 4-CF$_3$ | —CO—NH$_2$ |
| 2-OCH$_3$ | —CN |
| 2-OCH$_3$ | —CO—NH$_2$ |
| 2-OCF$_3$ | —CN |
| 2-OCF$_3$ | —CO—NH$_2$ |
| 2-OCHF$_2$ | —CN |
| 2,4-F$_2$ | —CN |
| 2,4-F$_2$ | —CO—NH$_2$ |
| 2-CH=N—OCH$_3$ | —CN |
| 4-CH=N—OCH$_3$ | —CN |
| 4-CH=N—OCH$_3$ | —CO—NH$_2$ |

If 2-(2-fluorobenzyl)-2-(1-cyano-cyclopropyl)-oxirane and 1,2,4-triazole are used as starting substances, the course of the process according to the invention can be illustrated by the following equation:

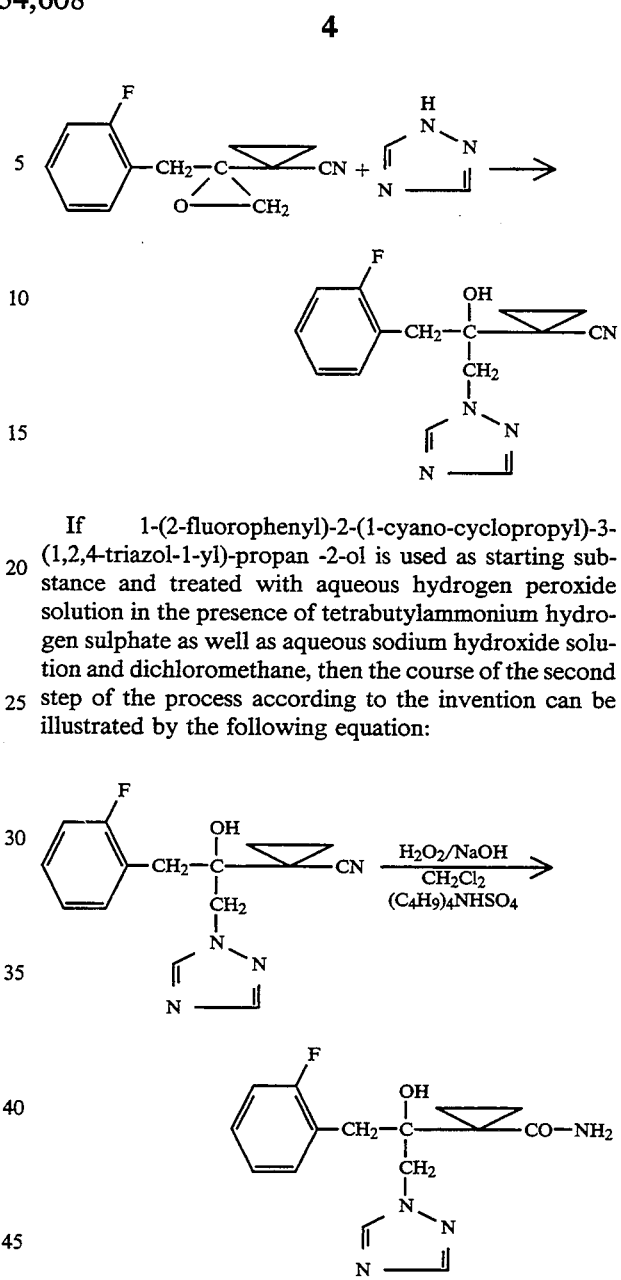

If 1-(2-fluorophenyl)-2-(1-cyano-cyclopropyl)-3-(1,2,4-triazol-1-yl)-propan -2-ol is used as starting substance and treated with aqueous hydrogen peroxide solution in the presence of tetrabutylammonium hydrogen sulphate as well as aqueous sodium hydroxide solution and dichloromethane, then the course of the second step of the process according to the invention can be illustrated by the following equation:

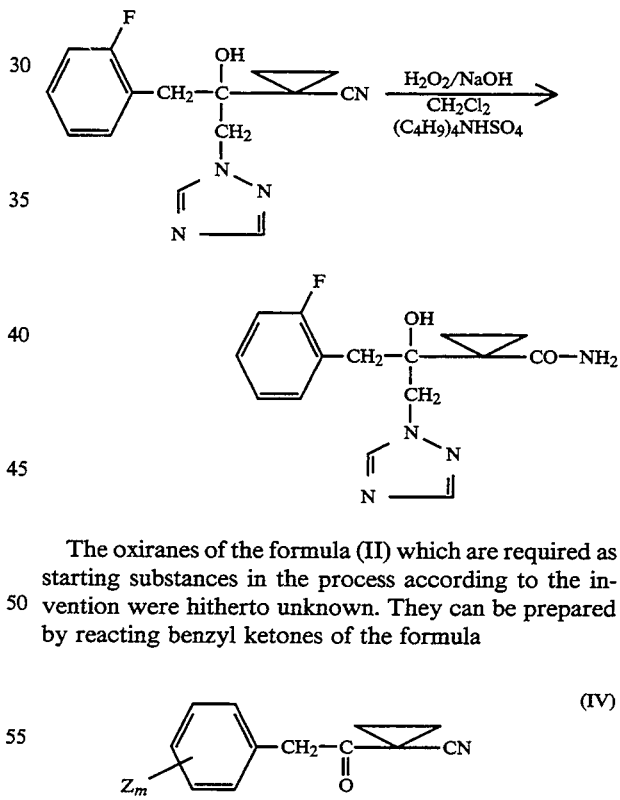

The oxiranes of the formula (II) which are required as starting substances in the process according to the invention were hitherto unknown. They can be prepared by reacting benzyl ketones of the formula

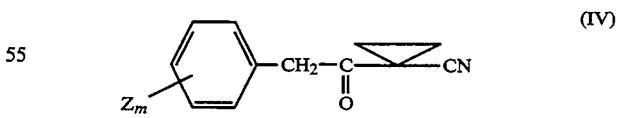

(IV)

in which

Z and m have the abovementioned meanings, either a) with dimethyloxosulphonium methylide, of the formula

(V)

or

β) with dimethylsulphonium methylide, of the formula

     (VI)

in the presence of a diluent.

The benzyl ketones of the formula (IV) can be prepared by a) reacting, in a first step, benzyl chlorides of the formula

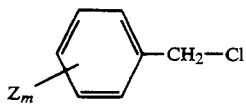     (VII)

in which

Z and m have the abovementioned meanings, with an excess of zinc powder in the presence of a diluent such as, for example, ethylene glycol dimethyl ether or tetrahydrofuran, at temperatures between 50° C. and 150° C. under a protective gas atmosphere, removing the excess zinc powder, and then, b) in a second step, reacting the resulting benzyl derivatives of the formula

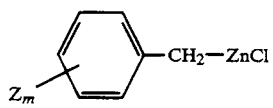     (VIII)

in which

Z and m have the abovementioned meanings, with 1-cyano-cyclopropyl-carboxylic acid chloride of the formula

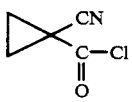     (IX)

in the presence of a palladium catalyst such as, for example, bis-(triphenylphosphine)-palladium-(II)-chloride, and in the presence of a diluent such as, for example, ethylene glycol dimethyl ether or tetrahydrofuran, at temperatures between 20° C. and 100° C. under a protective gas atmosphere.

The benzyl chlorides of the formula (VII) which are required as starting substances for carrying out the above process, and 1-cyano-cyclopropyl-carboxylic acid chloride of the formula (IX), which is required as reactant, are known or can be prepared by processes known in principle.

Dimethyloxosulphonium methylide, of the formula (V), which is required as reactant for carrying out variant (α) of the process for the preparation of the oxiranes of the formula (II), is known (cf. J. Am. Chem. Soc. 87, 1363–1364 (1965)). In the above reaction, it is processed in the freshly prepared state, by producing it in situ by reacting trimethyloxosulphonium iodide with sodium hydride or sodium amide, in particular with potassium tert.-butylate or sodium methylate, or by reacting trimethyloxosulfonium chloride with aqueous sodium hydroxide solution, in each case in the presence of a diluent.

Dimethylsulphonium methylide of the formula (VI), which is also suitable as reactant for carrying out variant (β) of the process for the preparation of oxiranes of the formula (II), is also known (cf. Heterocycles 8, 397 (1977)). In the above reaction, it also employed in the freshly prepared state, by preparing it in situ, for example from trimethylsulphonium halide or trimethyl-sulphonium methylsulphate, in the presence of a strong base such as, for example, sodium hydride, sodium amide, sodium methylate, potassium tert.-butylate or potassium hydroxide, in the presence of a diluent, such as tert.-butanol or dimethyl sulphoxide.

Suitable diluents for carrying out the above process for the preparation of oxiranes of the formula (II) are inert organic solvents. The following can preferably be used: alcohols, such as tert.-butanol, ethers such as tetrahydrofuran or dioxane, furthermore aliphatic and aromatic hydrocarbons such as benzene, toluene or xylene, as well as strong polar solvents such as dimethyl sulphoxides.

When carrying out the above process for the preparation of oxiranes of the formula (II), the reaction temperatures can be varied within a substantial range. In general, the process is carried out at temperatures between 0° C. and 100° C., preferably between 10° C. and 60° C.

When carrying out the above process for the preparation of oxiranes of the formula (II), 1 to 3 moles of dimethyloxosulphonium methylide of the formula (V), or dimethylsulphonium methylide, of the formula (VI), are generally employed per mole of benzyl ketone of the formula (IV). The oxiranes of the formula (II) are isolated by customary methods.

Suitable acid-binding agents for carrying out the first step of the process according to the invention are all customary inorganic and organic bases. The following can preferably be used: alkali metal carbonates, such as sodium carbonate and potassium carbonate, furthermore alkali metal hydroxides, such as sodium hydroxide and potassium hydroxide, moreover alkali metal alcoholates such as sodium methylate, sodium ethylate, potassium methylate and potassium ethylate as well as potassium tert.-butylate, and furthermore lower tertiary alkylamines, cycloalkylamines and aralkylamines, such as, in particular triethylamine.

Suitable diluents for carrying out the first step of the process according to the invention are all customary inert organic solvents. The following can preferably be used: nitriles such as acetonitrile, furthermore aromatic hydrocarbons such as benzene, toluene and dichlorobenzene, moreover formamides, such as dimethylformamide, as well as strongly polar solvents, such as dimethyl sulphoxide and hexamethylphosphoric triamide.

When carrying out the first step of the process according to the invention, the reaction temperatures can be varied within a substantial range. In general, the processes are carried out at temperatures between 0° C. and 200° C., preferably between 50° C. and 150° C.

When carrying out the first step of the process according to the invention, 1 to 4 moles of azole of the formula (III) and 1 to 2 moles of base are preferably employed per mole of oxirane of the formula (II). The end products are isolated in the customary manner.

When carrying out the second step of the process according to the invention, hydrogen peroxide is employed in the form of an aqueous solution. In general, a 30% strength aqueous solution of hydrogen peroxide is used.

Suitable phase transfer catalysts for carrying out the second step of the process according to the invention are all reaction accelerators which are customary for such purposes. The following can preferably be used: tetrabutylammonium chloride, tetrabutylammonium hydrogen sulphate, benzyl-triethyl-ammonium chloride and benzyl-triethyl-ammonium bromide.

Suitable aqueous alkali metal solutions for carrying out the second step of the process according to the invention are, preferably, sodium hydroxide solution and potassium hydroxide solution.

Suitable organic diluents for carrying out the second step of the process according to the invention are, preferably, aromatic hydrocarbons such as benzene or toluene, or halogenated aliphatic hydrocarbons such as dichloromethane or chloroform. When carrying out the second step of the process according to the invention, the reaction temperatures can also be varied within a substantial range. In general, the second step is carried out at temperatures between $-20°$ C. and $+60°$ C., preferably between $0°$ C. and $50°$ C.

When carrying out the second step of the process according to the invention, a procedure is followed in which an excess of aqueous hydrogen peroxide solution and a catalytic amount of a phase transfer catalyst as well as a small excess of aqueous alkali metal solution are employed per mole of compound of the formula (Ia). Working-up is carried out by customary methods.

The azolylmethyl-cyclopropyl derivatives of the formula (I) according to the invention can be converted into acid addition salts or metal salt complexes.

Suitable acids for the preparation of acid addition salts of compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent.

Suitable for the preparation of metal salt complexes of the compounds of the formula (I) are preferably those salts of metals which have already been mentioned in connection with the description of the metal salt complexes according to the invention as being preferred metal salts.

The metal salt complexes of the compounds of the formula (I) can be obtained in a simple manner by customary process, for example by dissolving the metal salt in alcohol, for example ethanol, and adding the solution to the compounds of the formula (I). Metal salt complexes can be isolated in a known manner, for example by filtration, and, if appropriate, purified by recrystallisation.

The active compounds according to the invention have a powerful microbicidal action and can be used as fungicides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by ways of limitation:

Xanthomonas species, such as *Xanthomonas oryzae*;
Pseudomonas species, such as *Pseudomonas lachrymans*;
Erwinia species, such as *Erwinia amylovora*;
Pythium species, such as *Pythium ultimum*;
Phytophthora species, such as *Phytophthora infestans*;
Pseudoperonospora species, such as *Pseudoperonospora humuli* or *Pseudoperonospora cubensis*; Plasmopara species, such as *Plasmopara viticola*;
Peronospora species, such as, *Peronospora pisi* or *P. brassicae*;
Erisiphe species, such as *Erisiphe graminis*;
Sphaerotheca species, such as *Sphaerotheca fuliginea*;
Podosphaera species, such as *Podosphaera leucotricha*;
Venturia species, such as *Venturia inaequalis*;
Pyrenophora species, such as *Pyrenophora teres* or *P. graminea*; (conidia form: Drechslera, syn: Helminthosporium);
Cochliobolus species, such as *Cochliobolus sativus*; (conidia form: Drechslera, syn: Helminthosporium);
Uromyces species, such as *Uromyces appendiculatus*;
Puccinia species, such as *Puccinia recondita*;
Tilletia species, such as *Tilletia caries*;
Ustilago species, such as *Ustilago nuda* or *Ustilago avenae*;
Pellicularia species, such as *Pellicularia sasakii*;
Pyricularia species, such as *Pyricularia oryzae*;
Fusarium species, such as *Fusarium culmorum*;
Botrytis species, such as *Botrytis cinerea*;
Septoria species, such as *Septoria nodorum*;
Leptosphaeria species, such as *Leptosphaeria nodorum*;
Cercospora species, such as *Cercospora canescens*;
Alternaria species, such as *Alternaria brassicae*, and
Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and *Pellicularia sasakii* on rice, and for combating diseases of cereals, such as *Leptosphaeria nodorum, Cochliobolus sativus, Pyrenophora teres, Pseudocercosporella herpotrichoides*, Erisphye and Fusarium species. Moreover, the substances according to the invention have a very good action against Venturia, Spaerotheca and Botrytis.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main, aromatics, such as xylene, toluene or alkylnaphthalenes, chlorinated aromatics or chlorinated aliphatic hydrocarbons, such as chlorobenzenes, chlorethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsuphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foes, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

On use of the substances according to the invention the application rate can be raised within a substantial range, depending on the type of the application method. For example, in the treatment of parts of plants, the active compound concentrations in the use forms, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of the soil, active compound concentrations of 0.00001 to 0.1% by weight, preferably 0.0001 to 0.02% by weight are required at the place of action.

The preparation and the use of the substances according to the invention can be seen from the examples which follow:

PREPARATION EXAMPLES

Example 1

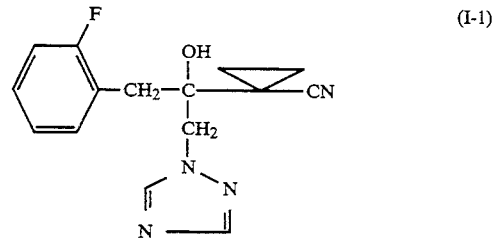
(I-1)

2.26 g (10.4mmol) of 2-(2-fluorobenzyl)-2-(1-cyanocyclo-propyl)-oxirane in 10 ml of dimethylformamide are added dropwise at 80° C. with stirring to a solution of 0.23 g (2.1 mmol) of potassium tert.-butylate and 2.15 g (31.2 mmol) of 1,2,4-triazole in 10 ml of dimethylformamide. When the addition has ended, stirring of the reaction mixture is continued for 4 hours at 80° C. The mixture is subsequently concentrated under reduced pressure, and the residue is taken up in ethyl acetate/water. The aqueous phase is extracted three times using ethyl acetate. The combined organic extracts are dried over sodium sulphate, concentrated under reduced pressure and chromatographed on silica gel using the eluent cyclohexane/ethyl acetate =1:1. 1.37 g (46% of theory) of 1-(2-fluorophenyl)-2-(1-cyanocyclopropyl)-3-(1,2,4-triazol-1-yl)-propan -2-ol are isolated.

$^1$H NMR (200 MHz, CDCl$_3$) : δ=0.4–1.1(m;4H), 3.2 (AB system; 2H), 4.12 (s; 1H), 4.5 (AB system; 2H), 7.05–7.45 (m; 4H), 7.0 (s; 1H), 8.33 (s; 1H).

PREPARATION OF STARTING SUBSTANCES

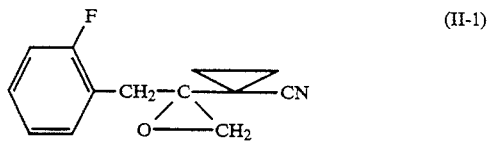
(II-1)

13.8 ml of 45% strength aqueous sodium hydroxide solution are added dropwise at room temperature in the course of 15 minutes to a suspension of 6.4 g (31.5 mmol) of 1-cyanocyclopropyl 2-fluorobenzyl ketone and 4.46 g (34.6 mmol) of trimethylsulphoxonium chloride in 30 ml of toluene. When the addition has ended, stirring of the reaction mixture is continued for 3 hours at room temperature and for one hour at 40° C. The reaction mixture is diluted with water, and the phases are separated. The aqueous phase is extracted three times using cyclohexane. The combined organic extracts are washed once with water, dried over sodium sulphate and concentrated under reduced pressure. The crude product is used for the further reaction without additional purification.

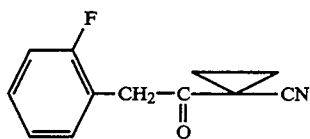
(IV-1)

A mixture of 32.7 g (0.5 mol) of zinc powder, 50.6 g (0.35 mol) of 2-fluoro-benzyl chloride and 375 ml of dry ethylene glycol dimethyl ether is refluxed for 2 hours under a nitrogen atmosphere. The reaction mixture is subsequently filtered under nitrogen. The filtrate is treated with 38.9 g (0.3 mol) of 1-cyano-cyclopropyl-carboxylic acid chloride and 21 mg (0.01 mol %) of bis-(triphenylphosphine)-palladium (II) chloride, and the mixture is refluxed for 2 hours under a nitrogen atmosphere. The reaction mixture is cooled to room temperature and then filtered, and the filtrate is concentrated under reduced pressure. The residue is taken up in toluene, the mixture is extracted by shaking with dilute aqueous hydrochloric acid, the organic phase is dried, and the solvent is stripped off under reduced pressure.

The residue which remains is subjected to fractional distillation. 56.9 g of an oil which, according to gas chromatogram, consists to 90% of 1-cyano-cyclopropyl 2-fluoro-benzyl ketone, are obtained. Accordingly, the yield is calculated as 84 % of theory.

Example 2

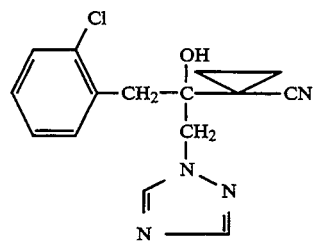
(I-2)

Compound (I-2) is also prepared by the method in Example 1.

$^1$H NMR (200 MHz, CDCl$_3$) : δ=0.3–1.1(m; 4H), 3.2 (AB system; 2H), 4.5 (AB system; 2H), 7.1–7.5 (m; 4H), 7.96 (s; 1H), 8.31 (s; 1H).

PREPARATION OF STARTING SUBSTANCES

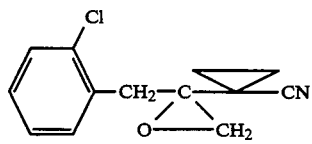
(II-2)

10 ml of 45% strength aqueous sodium hydroxide solution are added dropwise at room temperature in the course of 15 minutes to a suspension of 5 g (22.76 mmol) of 1-cyanocyclopropyl 2-chlorobenzyl ketone and 3.22 g (25.04 mmol) of trimethylsulphoxonium chloride in 25 ml of toluene. When the addition has ended, stirring of the reaction mixture is continued for 3 hours at room temperature and for one hour at 40° C. The reaction mixture is diluted with water and the phases are separated. The aqueous phase is extracted three times using cyclohexane. The combined organic extracts are washed once with water, dried over sodium sulphate and concentrated under reduced pressure. The crude product is used for the further reaction without additional purification.

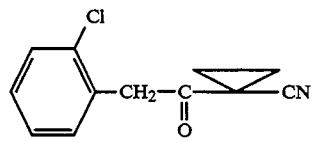
(IV-2)

A mixture of 32.7 g (0.5 mol) of zinc powder, 56.4 g (0.35 mol) of 2-chloro-benzyl chloride and 375 ml of dry ethylene glycol dimethyl ether is refluxed for 2 hours under a nitrogen atmosphere. The reaction mixture is subsequently filtered under nitrogen. The filtrate is treated with 38.9 g (0.3 mol) of 1-cyano-cyclopropyl-carboxylic acid chloride and 31 mg (0.01 mol %) of bis-(tri-phenylphosphine)-palladium (II) chloride and the mixture is refluxed for 2 hours under a nitrogen atmosphere. The reaction mixture is cooled to room temperature and then filtered, and the filtrate is concentrated under reduced pressure. The residue is taken up in toluene, extracted by shaking with dilute aqueous hydrochloric acid, the organic phase is dried, and the solvent is stripped off under reduced pressure. The residue which remains is subjected to fractional distillation. 58.7 g of an oil which, according to gas chromatogram, consists of 90 % of 1-cyano-cyclopropyl 2-chlorobenzyl ketone, are obtained. Accordingly, the yield is calculated as 80 % of theory.

In the use examples which follow, the compounds of the formulae listed below were employed as comparison substances:

(A)

(B)

(Disclosed in EP-OS (European Published Specification) 0,106,515)

Example A

Erysiphe test (barley)/protective
Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp.hordei.

The plants are placed in a greenhouse at a temperature of approx. 20° C. and a relative atmospheric humidity of approx. 80% to favour the development of mildew pustules.

The test is evaluated 7 days after inoculation.

In this test, a degree of effectiveness of 100% is shown, at a concentration of 250 ppm, in the spraying liquid, by compound (I-2) according to the invention.

Example B

Erysiphe test (wheat)/protective
Solvent: 100 parts by weight of dimethylformamide
Emulsifier: 0.25 parts by weight of alkylaryl polyglycol ether To prepare a suitable preparation of active compound, 1 part by weight of active compound is mixed with the stated Mounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. tritici.

The plants are placed in a greenhouse at a temperature of approx. 20° C. and a relative atmospheric humidity of approx. 80% to favour the development of mildew pustules.

The test is evaluated 7 days after inoculation.

In this test, a degree of effectiveness of 100% is shown, at the concentration of 250 ppm, in the spraying liquid, by compound (I-2) according to the invention, whereas the comparison substance shows a degree of effectiveness of 85%.

Example C

Fusarium nivale (vat. nivale) test (wheat)/protective
Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Fusarium nivale (vat. nivale).

The plants are covered with transparent incubation cloches in a greenhouse at a temperature of approx. 15° C. and a relative atmospheric humidity of approx. 100%.

The test is evaluated 4 days after inoculation.

In this test, a degree of effectiveness of 100% is shown, at a concentration of 250 ppm, in the spraying liquid, by compound (I-2) according to the invention, whereas the comparison substance (A) does not show any activity.

Example D

Fusarium nivale (vat. majus) test (wheat)/protective
Solvent: 100 parts by weight of dimethylformamide
Emulsifier: 0.25 parts by weight of alkylaryl-polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Fusarium nivale (vat. majus).

The plants are covered with transparent incubation cloches in a greenhouse at a temperature of approx. 15° C. and a relative atmospheric humidity of approx. 100%.

The test is evaluated 4 days after inoculation.

In this test, a degree of effectiveness of 100% is shown, 1, at a concentration of 250 ppm, in the spraying liquid, by compound (I-2) according to the invention, whereas the comparison substance (A) does not show any activity.

Example E

Fusarium culmorum test (wheat)/protective
Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidiea suspension of Fusarium culmorum.

The plants are covered with transparent incubation cloches in a greenhouse at a temperature of approx. 20° C. and a relative atmospheric humidity of approx. 100%.

The test is evaluated 4 days after inoculation.

In this test, a degree of effectiveness of 100% is shown, at a concentration of 250 ppm, in the spraying liquid, by compound (I-2) according to the invention, whereas the comparison substance (A) does not show any activity.

Example F

Uncinula test (vines)/protective
Solvent: 4.7 parts by weight of acetone
Emulsifier: 0.3 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Uncinula necator.

The plants are then placed in a greenhouse at 23 to 24° C. and at a relative atmospheric humidity of about 75%.

Evaluation is carried out 14 days after the inoculation.

In this test, a degree of effectiveness of 100% is shown, at a concentration of 1 ppm in the spraying liquid, by compound (I-1) according to the invention.

Example G

Pyricularia Test (rice)/protective
Solvent: 12.5 parts by weight of acetone
Emulsifier: 0.3 parts by weight of alkylarylpolyglycolether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100 % relative atmospheric humidity and 25° C.

Evaluation of the disease infestation is carried out 4 days after the inoculation.

In this test, the compounds (I-1) and (I-2) according to the invention, at a concentration of 0,025% in the spraying liquid, show a degree of activity of 80% and higher, whereas the comparison substance (A) shows a degree of activity of 30%.

Example H

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore Suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, the compounds (I-1) and (I-2) according to the invention, at an amount of 100 mg/100 cm$^2$, show a degree of activity of 80% and higher, whereas the comparison substance (A) shows a degree of activity of 70%.

Example I

Leptosphaeria nodorum test (wheat)/protective
Solvent: 100 parts by weight of dimethylformamide
Emulsifier: 0. 25 parts by weight of alkylaryl polyglycol ether To produce a suitable preparation of active compound, 1 part by weight of active compound is mixed with the stated amounts of solvent and emulsifier, and the concentrate is diluted with water to desired concentration.

To test For protective activity, young plants are sprayed with the preparation of active compound until dew-moist. After the spray coating has dried on, the plants are sprayed with a spore suspension of Leptosphaeria nodorum.

The plants then remain in an incubation cabin at 20° C. and 100% relative atmosphaeric humidity for 48 hours.

The plants are placed in a greenhouse at a temperature of about 15° C. and a relative atmospheric humidity of about 80%.

Evaluation is carried out 10 days after the inoculation.

In this test, the compound (I-2) according to the invention, at a concentration of 250 ppm in the spraying liquid, shows a degree of activity of 85%, whereas the comparison substance (A) shows a degree of activity of 18%.

Example K

Pyrenophora teres test (barley)/protective
Solvent: 100 parts by weight or dimethylformamide
Emulsifier: 0.25 parts by weight of alkylaryl polyglycol ether To produce a suitable preparation of active compound, 1 part by weight or active compound is mixed with the stated amounts of solvent and emulsifier, and the concentrate is diluted with water to desired concentration.

To test for protective activity, young plants are sprayed with the preparation or active compound until dew-moist. After the spray coating has dried on, the plants are sprayed with a conidia suspension of Pyrenophora teres.

The plants then remain in an incubation cabin at 20° C. and 100% relative atmosphaeric humidity for 48 hours.

The plants are placed in a greenhouse at a temperature of about 20° C. and a relative atmospheric humidity or about 80%.

Evaluation is carried out 7 days after the inoculation.

In this test, the compound (I-2) according to the invention, at a concentration of 250 ppm in the spraying liquid, shows a degree of activity of more than 70%, whereas the comparison substance (A) does not show any activity.

It is understood that the specification and examples are illustrative but not limitative of the present invention and that other embodiments within the spirit and scope of the invention will suggest themselves to those skilled in the art.

What is claimed is:

1. A compound wherein such compound is 1-(2-chlorophenyl)-2-(1-cyano-cyclo-propyl) -3-(1,2,4-triazol-1-yl)-propan-2-ol of the formula.

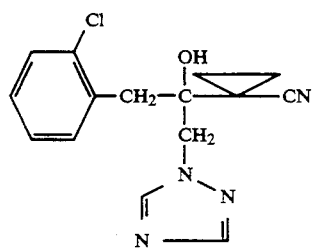
2. A fungicidal composition comprising a fungicidally effective amount of a compound or addition product according to claim 1 and an inert diluent.
3. A method of combating fungi, which method comprises applying to such fungi or to their habitat a fungicidally effective amount of a compound or addition product according to claim 1.
* * * * *